US00PP33495P2

(12) United States Plant Patent
Ward et al.

(10) Patent No.: US PP33,495 P2
(45) Date of Patent: Sep. 21, 2021

(54) APPLE TREE NAMED 'EASTMAN'

(50) Latin Name: *Malus domestica*
Varietal Denomination: Eastman

(71) Applicants: Rafe Douglas Ward, Wheeler, MI (US); Nicole Elizabeth Ward, Wheeler, MI (US)

(72) Inventors: Rafe Douglas Ward, Wheeler, MI (US); Nicole Elizabeth Ward, Wheeler, MI (US)

( * ) Notice: Subject to any disclaimer, the term of this patent is extended or adjusted under 35 U.S.C. 154(b) by 0 days.

(21) Appl. No.: 16/974,141

(22) Filed: Oct. 16, 2020

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 6/7418
See application file for complete search history.

*Primary Examiner* — Anne Marie Grunberg
(74) *Attorney, Agent, or Firm* — Michelle Bos Legal LLC

(57) ABSTRACT

'Eastman' is a new variety of apple tree discovered as a chance seedling. The fruit of 'Eastman' is notable for its attractive tri-color flesh.

4 Drawing Sheets

Latin name: *Malus domestica.*
Variety denomination: 'Eastman'.

BACKGROUND OF THE VARIETY

'Eastman' is a new and distinct apple tree of unknown parentage, discovered as a chance seedling in a cultivated orchard at Wheeler, Mich. 'Eastman' was first observed in 2012, and was first asexually reproduced by bud grafting in 2014 in the same location. The variety has since been asexually reproduced by budding, and has been observed to remain true to type over successive asexually propagated generations.

BRIEF DESCRIPTION OF THE VARIETY

The 'Eastman' apple tree was first selected for its distinctive fruit, which consistently exhibits an intense red overcolor and an attractive tri-color flesh including hues of yellow and dark to light red. Fruit of the 'Eastman' apple tree can be distinguished from fruit of the 'Pink Pearl' apple tree (U.S. Plant Pat. No. 723) by its larger size and intense red overcolor as compared to the smaller size and blushed pale green of 'Pink Pearl'. The fruit of the 'Eastman' apple tree is further distinguished by its brown stem and pronounced crown as compared to the green stem and an more rounded stem of 'Pink Pearl' apples.

BRIEF DESCRIPTION OF THE PHOTOGRAPHS

The attached photographs were taken during the 2019 and 2020 growing seasons near East Wenatchee, Wash. The trees shown were planted in 2018 on 'M26' rootstock (not patented).

DETAILED BOTANICAL DESCRIPTION OF THE VARIETY

Figure 1:
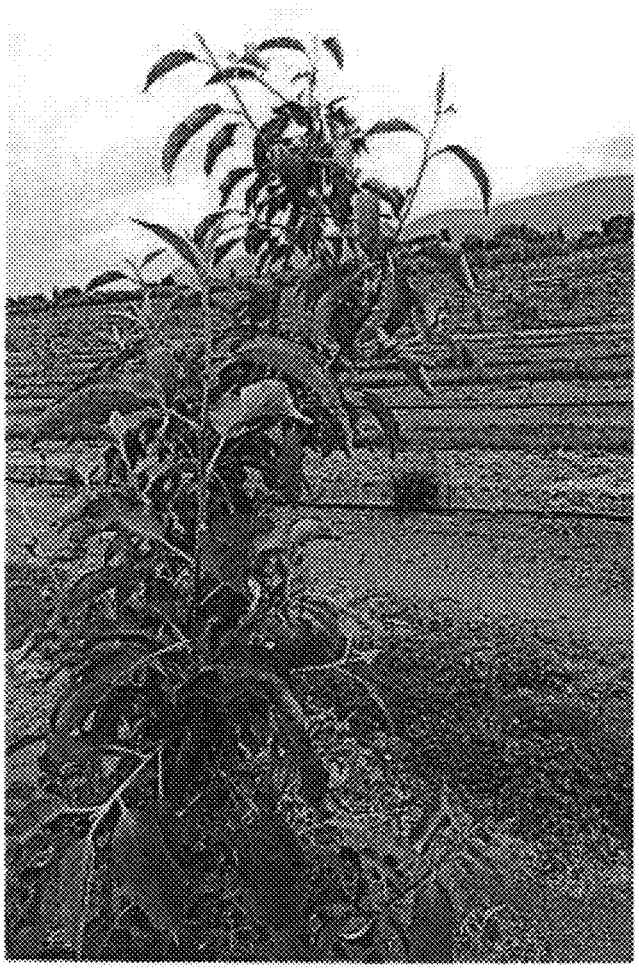
FIG. 1 shows an 'Eastman' apple tree.
Figure 2:
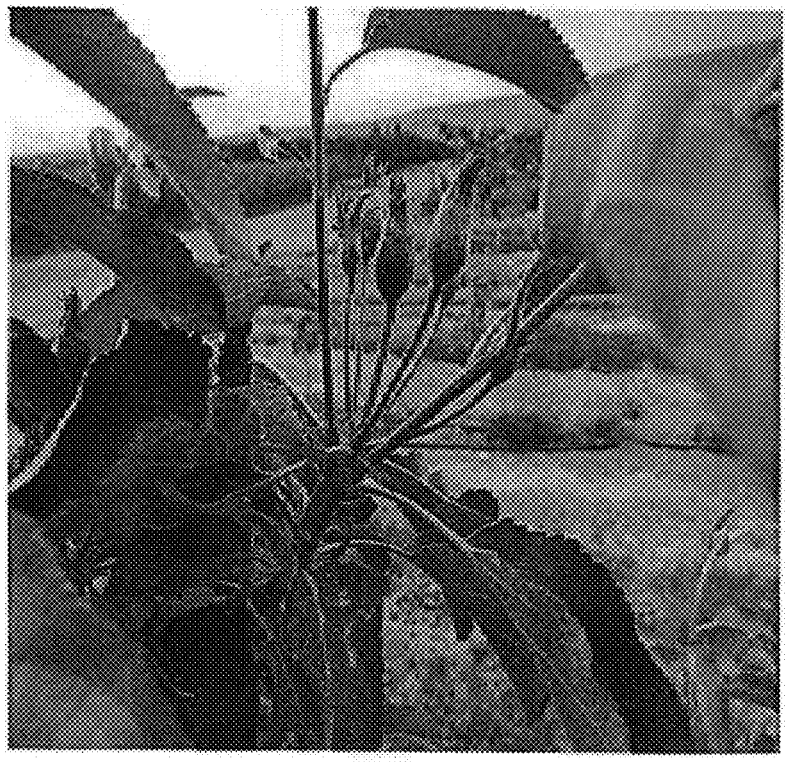
FIG. 2 shows buds and leaves on an 'Eastman' apple tree.
Figure 3:
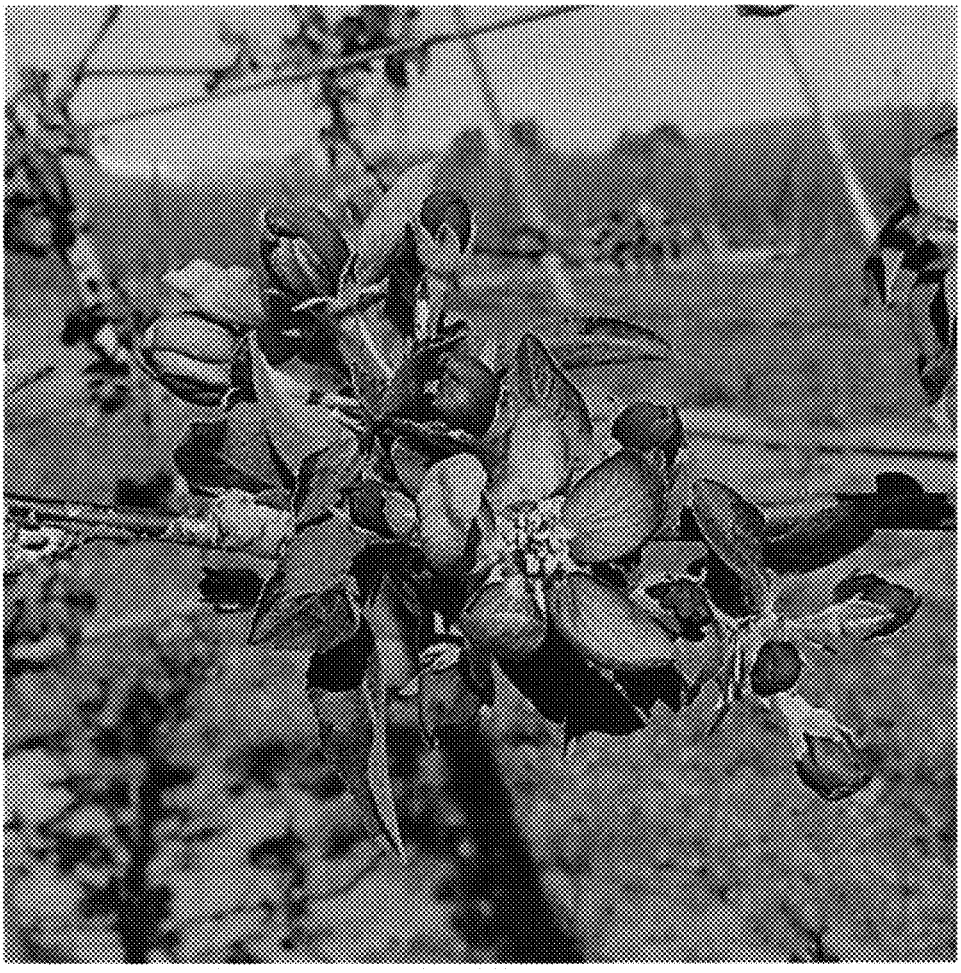
FIG. 3 shows flowers and leaves on an 'Eastman' apple tree.
Figure 4:
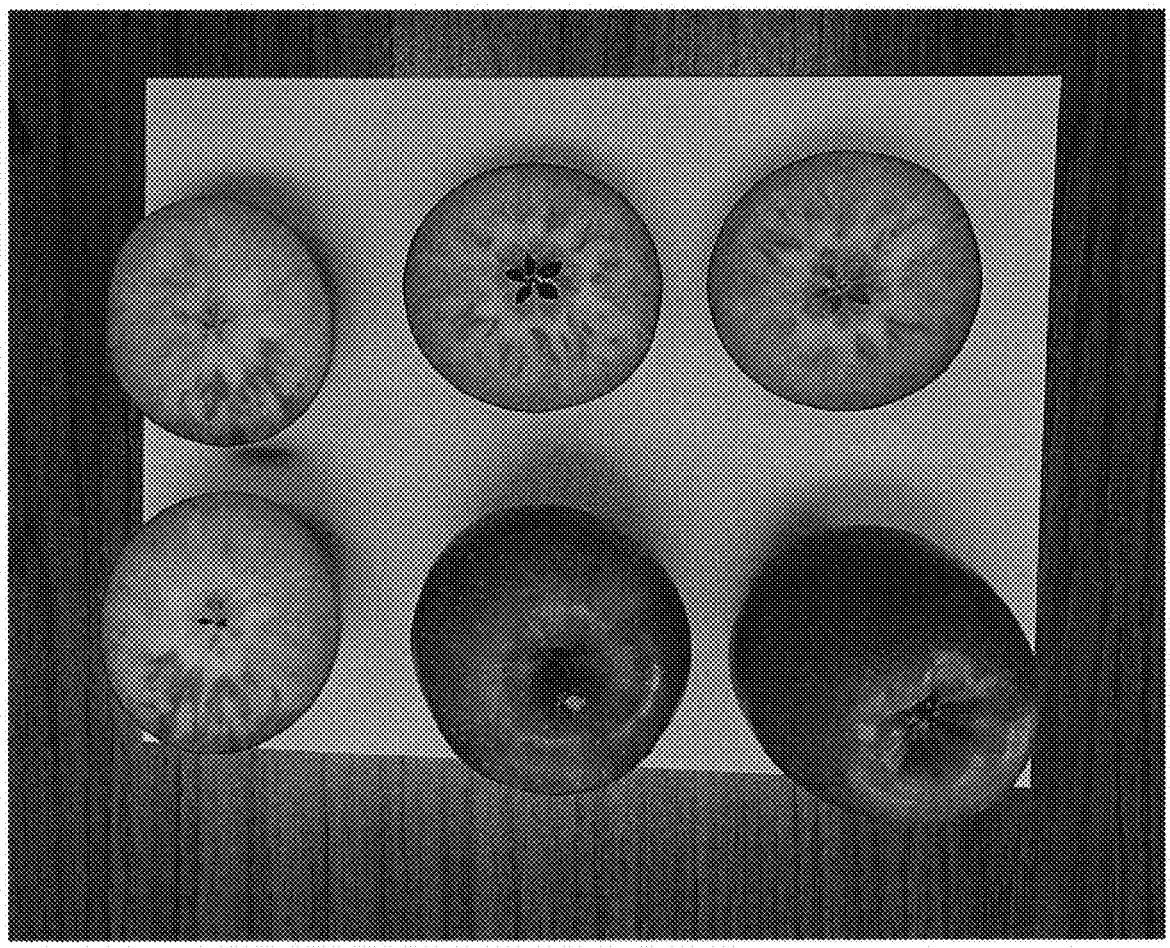
FIG. 4 shows whole and sectioned fruit of the 'Eastman' apple variety.

The following botanical description is based primarily on observations made during the 2019 and 2020 growing seasons near East Wenatchee, Wash. of three-year-old trees planted on 'M26' rootstock. It should be understood that the characteristics described will vary somewhat depending upon cultural practices and climatic conditions, and will vary with location and season. Colors are described with reference to the Munsell Book of Color.

Tree:
- *Vigor.*—Moderate.
- *Type.*—Slender spindle supported.
- *Habit.*—Upright, spreading.
- *Height.*—2 m to 3 m.
- *Trunk diameter at* 30 *cm above graft.*—4 cm.
- *Bearing.*—On spurs.
- *Bark texture.*—Smooth, pubescent.
- *Bark color.*—Medium gray purple 6.5 RY 7/10, influenced by pubescence.
- *Lenticel size.*—1.5 mm to 3 mm diameter.
- *Lenticel color.*—Pale yellow gray 2.5 Y 8.5/2.

Branch (fruiting branches located at around 1 m above the graft union):
- *Length.*—115 cm.
- *Diameter.*—5 mm to 10 mm.
- *Crotch angle.*—80°.
- *Bark color.*—Purple brown 7.5 R 3/2.
- *Lenticel size.*—2 mm to 4 mm long.
- *Lenticel color.*—Pale yellow 2.5 Y 8.5/4.
- *Lenticel density.*—1 to 2 per $cm^2$.

One year old shoot:
- *Length.*—46 cm.
- *Diameter.*—4 mm to 6 mm.
- *Pubescence.*—Lightly pubescent, fine short hairs.
- *Growth pattern.*—Straight.

*Shoot.*—Color Gray 5R 7/2 with pubescence; Dark purple 5R 3/2 without pubescence.
*Internode length.*—Average 25 mm.
*Lenticel density.*—1.3 per $cm^2$.
*Vegetative bud position.*—Tight, not held out.
*Vegetative bud apex shape.*—Pointed.

Flower buds:
*Bud shape.*—Ovate.
*Quantity per spur.*—3 to 5.
*Length.*—15 mm.
*Diameter.*—5 mm.
*Color.*—Pink 7.5RP 4/8.

Flowers:
*Date of first bloom.*—Around Apr. 10, 2020.
*Date of full bloom.*—Around Apr. 17, 2020.
*Inflorescence type.*—Umbellate.
*Diameter of fully open flower.*—Medium, 40 mm.
*Flower shape.*—Shallow cup.
*Relative position of petal margin.*—Not touching.
*Number of petals per flower.*—5.
*Petal length.*—3 cm to 4 cm.
*Petal width.*—1.5 cm.
*Petal shape.*—Ovate.
*Apex shape.*—Rounded.
*Base shape.*—Narrow.
*Margin.*—Smooth.
*Petal vein prominence.*—Prominent.
*Petal color.*—Pink purple 2.5 RP 4/8 (both surfaces).
*Pistils.*—Length 15 mm; white.
*Stigma.*—Diameter 0.5 mm; white.
*Style.*—Length 15 mm; white.
*Ovary.*—Length 2.5 mm; white.
*Position of stigmas relative to anthers.*—Above.
*Anthers.*—4 to 8 per flower; length 15 mm.
*Pollen.*—Present; Bright yellow 7.5Y 7/10.
*Pedicel length.*—3 cm to 4 cm.
*Pedicel diameter.*—1.5 mm.
*Pedicel color.*—Gray green 5GY 6/6.
*Number of sepals.*—5 per blossom.
*Sepal shape.*—Acute.
*Sepal margin.*—Smooth.
*Sepal color.*—Yellow 10Y 6/2.

Leaves:
*Shape.*—Elliptic.
*Profile in cross-section.*—Mildly convex.
*Length.*—Long, 8 cm to 11 cm, average 10 cm.
*Width.*—Narrow, 3.5 cm to 4.5 cm, average 4 cm.
*Length/width ratio.*—Large 8:3.
*Blade margin.*—Finely crenate, little or no undulation.
*Apex shape.*—Acuminate.
*Base shape.*—Obtuse.
*Color of upper surface.*—Primary leaves dark green 2.5GY 3/4; terminal leaves maroon 5R 3/4 (observed Sep. 29, 2019).
*Color of lower surface.*—Primary leaves medium green 2.5GY 5/4; terminal leaves lavender 5R 5/2 (observed Sep. 29, 2019).
*Pubescence of lower surface.*—Strong.
*Attitude in relation to shoot.*—Upwards.
*Petiole length.*—6 mm.
*Petiole color.*—Dark red maroon 7.5 R 3/4.

Fruit:
*Quantity per cluster.*—Originally 2 to 3; thinned to 1.
*Diameter.*—6.5 cm to 7.5 cm.
*Height.*—6 cm to 8 cm.
*Weight.*—112 g to 225 g, average 186 g.
*Ratio of height to width.*—1:1.
*General shape in profile.*—Slightly elongated, with a few tending toward globose.
*Position of maximum diameter.*—Between equator and upper third.
*Ribbing.*—Absent.
*Crowning at calyx end.*—Somewhat to profoundly crowned.
*Size of eye.*—5 mm.
*Aperture of eye.*—Closed.
*Length of sepal.*—3 mm to 4 mm.
*Bloom of skin.*—Not present.
*Greasiness of skin.*—Absent.
*Anthocyanin coloration of young fruit.*—Intense.
*Background color of skin.*—Yellow 2.5 Y 8/10.
*Over color of skin.*—Medium red 5 R 5/10 to dark red 5 R 3/10.
*Amount of over color.*—Very high, 95%.
*Intensity of over color.*—Intense.
*Pattern of over color.*—Patchy with some streaking; slightly netted; lenticels prominent.
*Lenticel color.*—Pale yellow 2.5Y 9/2.
*Lenticel diameter.*—1.5 mm.
*Lenticel density.*—5 per $cm^2$.
*Amount of russet around stalk cavity.*—Slight.
*Amount of russet on cheeks.*—None.
*Area of russet around eye basin.*—Absent or slight.
*Length of stalk.*—10 mm to 30 mm.
*Thickness of stalk.*—3 mm to 5 mm, with enlarged distal end.
*Stalk color.*—*Brown* 7.5 YR 4/6.
*Depth of stalk cavity.*—15 mm.
*Width of stalk cavity.*—25 mm.
*Depth of eye basin.*—12 mm to 15 mm.
*Width of eye basin.*—35 mm to 37 mm.
*Firmness of flesh.*—Tender to medium firm.
*Flesh texture.*—Somewhat coarse.
*Juiciness.*—Slightly juicy.
*Brix.*—18.5 to 20.5° Brix, average 19° Brix.
*Flesh color.*—Tri-colored, dark red 10 RP 5/12 to light red 5 R 5/10, and pale yellow 7.5 YR 9/2; 60% to 90% of flesh is red, average 85% red.
*Aperture of locules in cross section.*—Moderately open.

Seeds:
*Quantity of seeds per fruit.*—About 10, similar to 'Tenroy Gala'.
*Shape.*—Teardrop.
*Color.*—Dark brown 7.5 YR 3/4.
*Eating quality of fruit.*—Excellent.
*Harvest maturity.*—Early (Sep. 1, 2019).
*Number of picks.*—2 picks, five days apart.
*Yield.*—35 fruits per tree (3-year-old tree).
*Resistance to pests and diseases.*—Unknown.
*Storageability.*—2019 crop stored well for 4 months in typical cold storage conditions.

Market use: Fresh and processed.

The invention claimed is:

1. We claim a new and distinct apple tree substantially as described and illustrated herein.

* * * * *